United States Patent [19]

Nychka et al.

[11] 4,155,941
[45] May 22, 1979

[54] DECHLORINATION OF HALOETHANES USING ETHYLENE

[75] Inventors: Henry R. Nychka, East Aurora; Richard E. Eibeck, Orchard Park, both of N.Y.

[73] Assignee: Allied Chemical Corporation, Morris Township, Morris County, N.J.

[21] Appl. No.: 855,147

[22] Filed: Nov. 28, 1977

[51] Int. Cl.$^2$ .............................................. C07C 21/18
[52] U.S. Cl. ................................................... 260/653.5
[58] Field of Search ..................................... 260/653.5

[56] References Cited

U.S. PATENT DOCUMENTS 3,697,608  10/1972  Bellis ................................. 260/653.5

Primary Examiner—C. Davis
Attorney, Agent, or Firm—Alan M. Doernberg; Jay P. Friedenson

[57] ABSTRACT

A haloethane is dechlorinated by reacting in the gaseous phase a haloethane selected from $CCl_2FFCClF_2$, $CClF_2CClF_2$ and $CCl_2FCCl_2F$ with ethylene in the presence of a transition metal catalyst selected from iron, nickel, vanadium and chromium oxides, chlorides and fluorides and recovering a perhaloethylene and vinyl chloride. Perhaloethylenes are used as monomers for halogenated polymers. Vinyl chloride is also a widely used monomer.

15 Claims, No Drawings

DECHLORINATION OF HALOETHANES USING ETHYLENE

BACKGROUND OF THE INVENTION

Perhaloethylenes such as monochlorotrifluoroethylene or tetrafluoroethylene are presently prepared by dechlorination of the corresponding haloalkenes such as 1,1,2-trichloro-1,2,2-trifluoroethane or 1,2-dichlorotetrafluoroethylene with zinc metal in alcohol. Suggestions have been made to dechlorinate with hydrogen or hydrogen supplying materials in the vapor phase, with another haloalkene and reduced salt melts as the chlorine acceptor.

The present zinc process consumes expensive zinc and gives a moderate product yield. The various proposed processes either consume expensive materials, give low conversion or both.

BRIEF DESCRIPTION OF THE INVENTION

The invention includes a method for the dechlorination of haloethanes comprising reacting in the gaseous phase a haloethane selected from the group consisting of $CCl_2FCClF_2$, $CClF_2CClF_2$ and $CCl_2FCCl_2F$ with ethylene in the presence of a transition metal catalyst selected from the group consisting of iron, nickel, vanadium and chromium oxides, chlorides and fluorides and recovering a perhaloethylene and vinyl chloride.

DETAILED DESCRIPTION OF THE INVENTION

The present invention is concerned with a process for the alpha, beta dechlorination of a haloethane by reaction with ethylene in the presence of a catalyst. Preferred halohydrocarbons include 1,2-dichlorotetrafluoroethane (known as fluorocarbon 114) and 1,1,2-trichloro-1,2,2-trifluoroethane (known as fluorocarbon 113). When two chlorines are removed from these preferred halohydrocarbons, the product perhaloethylenes are tetrafluoroethylene (fluorocarbon 1114) and chlorotrifluoroethylene (fluorocarbon 1113), which are important fluoropolymer monomers. Fluorocarbon 112 may also be converted to fluorocarbon 1112.

Using ethylene as the other reactant the byproducts are vinyl chloride, itself useful as a polymer monomer, and HCl. The byproduct HCl may add across one of the double bonds of product or byproduct vinyl chloride. Ethylene may also be directly converted to 1,2-dichloroethane. However, under most reaction conditions, any 1,2-dichloroethane formed in situ is converted to vinyl chloride by HCl elimination.

The temperature of the reaction is not critical, with various combinations of catalyst, haloethane and ethylene exhibiting different temperature ranges for some reaction rate and for maximum reaction rate. Obviously, in order to have reaction in the gaseous phase, the temperature and pressure must be such that all reactants are in the vapor phase. Also, clearly, temperatures at or above the decomposition temperatures of reactants and products cannot be used. Preferred temperatures, especially for the reaction between ethylene and fluorocarbon 113 or 114, are between about 400° C. and about 600° C. with between about 400° and about 500° C. being more preferred and between about 450° C. and about 500° C. being most preferred.

The pressure of the reaction is not critical, although substantially atmospheric pressures are preferred. The molar ratio of haloethane:ethylene is not critical but is preferably between about 0.1:1 and about 10:1 with between about 0.5:1 and about 2:1 being more preferred.

The contact time is not critical so long as the reactants are in contact with the catalyst sufficiently long for reaction to occur. Contact times of about 0.3 to about 60 seconds are preferred since little yield improvement is likely to occur with greater contact times, and more preferred contact times are between about 3 and about 6 seconds.

The catalyst must be a transition metal oxide or halide which actively catalyzes the present reaction. As shown in the examples that follow, a broad range of materials are somewhat active. The catalysts of the present invention which are especially active include oxides, fluorides and chlorides of iron, nickel, vanadium and chromium. They may be applied to an inert support, as for example at a rate of between about 0.003 and about 0.30 moles of oxide, fluoride or chloride per 100 grams of support. By "inert" is meant that the support is not significantly decomposed under reaction conditions which normally includes some HF from side reactions. The support may itself have catalytic activity, as for example magnesium chloride or fluoride supports, or may include promoter materials such as alkali halides. Materials such as alpha or gamma alumina are less preferred as supports since they do react with HF to an extent.

The preferred catalyst materials includes oxides such as iron (II) oxide, iron (III) oxide, nickel (II) oxide, vanadium (II) oxide, and chromium (III) oxide. They also include chlorides such as iron (II) chloride, iron (III) chloride, nickel (II) chloride, vanadium (IV) chloride, vanadium (II) chloride, chromium (III) chloride and chromium (II) chloride and the corresponding fluorides. Preferred catalyst also include oxychlorides and oxyfluorides such as CrOF, FeOCl and the like, which represent partially fluorinated or chlorinated oxides.

More preferred are the iron compounds at valence state 3, including iron (III) oxide, iron (III) chloride and iron (III) fluoride, as well as partially chlorinated or fluorinated oxides. Most preferred is iron (III) chloride.

Especially preferred combinations of catalyst and support include iron (III) chloride on sodium magnesium fluoride, iron (III) chloride on potassium magnesium fluoride, iron (III) chloride on gamma aluminum fluoride and iron (III) chloride on chromium (III) oxide.

COMPARATIVE

EXAMPLE 1

0.3 moles of copper (II) chloride is applied to 100 grams of $Al_2O_3$ support particles of 10–20 mesh size (American standard mesh size), by dissolving the chloride in about 50 milliliters of water and adding the solution to an evacuated flask containing the support particles. The sample was then dried overnight at 100° C. A 100 milliliter portion of the sample was charged to a three-fourths inch inside diameter, 20 inch long stainless steel reactor immersed in a temperature controlled sand bath at 400° C., 450° C. and 500° C. 1.44 moles/hour of ethylene and 0.72 moles/hour of trichlorotrifluoroethane (fluorocarbon 113 or $CCl_2FCClF_2$) were fed into the reactor giving a contact time of 3.3 seconds. After one hour, the effluent was analyzed by on-line gas chromatography. The results are shown in Table 1 indicating a greatest conversion of fluorocarbon 113 at 500° C. (58%) with 72% of the reacted 113 going to $C_2ClF_3$ (fluorocarbon 1113) and 0.64 being the ratio of vinyl chloride/fluorocarbon 1113.

EXAMPLES 2-10

Example 1 was repeated using each of the chlorides on an $Al_2O_3$ base shown in Table 1. Conversion of fluorocarbon 113 was highest in Example 6 for iron (III) chloride (98%) with 95% yield and a ratio of 0.36. Examples 2, 3, 6 and 7 represent the use of catalysts of the present invention. The remainder (designated C for comparative) represent other catalyst materials.

Table 1

Reaction of $C_2Cl_3F_3$ and $C_2H_4$
Contact Time 3.3 Seconds

| Example | Catalyst | Temperature | % Conversion* of $C_2Cl_3F_3$ | % Yield** $C_2ClF_3$ | Ratio*** |
|---|---|---|---|---|---|
| C1 | Copper (II) chloride on $Al_2O_3$ | 400 | 9 | 53 | 0.50 |
|  |  | 450 | 30 | 71 | 0.30 |
|  |  | 500 | 58 | 72 | 0.64 |
| 2 | Chromium chloride on $Al_2O_3$ | 400 | 6 | 48 | 0.17 |
|  |  | 450 | 23 | 71 | 0.35 |
|  |  | 500 | 41 | 92 | 0.42 |
| 3 | Nickel chloride on $Al_2O_3$ | 400 | 20 | 8 | 0.70 |
|  |  | 450 | 43 | 32 | 0.57 |
|  |  | 500 | 50 | 85 | 0.24 |
| C4 | Manganese chloride on $Al_2O_3$ | 450 | 36 | 71 | 0.18 |
| C5 | Cobalt chloride on $Al_2O_3$ | 400 | 15 | 8 | 0.69 |
|  |  | 450 | 35 | 89 | 0.07 |
|  |  | 500 | 29 | 88 | 0.17 |
| 6 | Iron chloride on $Al_2O_3$ | 400 | 48 | 41 | 0.85 |
|  |  | 450 | 83 | 71 | 0.50 |
|  |  | 500 | 98 | 95 | 0.36 |
| 7 | Vanadium chloride on $Al_2O_3$ | 400 | 7 | 24 | 0.00 |
|  |  | 450 | 38 | 81 | 0.46 |
|  |  | 500 | 86 | 93 | 0.05 |
| C8 | Palladium chloride on $Al_2O_3$ | 400 | 7 | 75 | 0.13 |
|  |  | 450 | 30 | 85 | 0.06 |
|  |  | 500 | 42 | 87 | 0.05 |
| C9 | Cerium chloride on $Al_2O_3$ | 400 | 5 | 42 | 0.08 |
|  |  | 450 | 24 | 82 | 0.21 |
|  |  | 500 | 90 | 81 | 0.07 |
| C10 | Zinc chloride on $Al_2O_3$ | 400 | 5 | 68 | 0.00 |
|  |  | 450 | 39 | 80 | 0.03 |
|  |  | 500 | 90 | 81 | 0.07 |

*By "% Conversion" is moles $C_2Cl_3F_3$ consumed/moles $C_2Cl_3F_3$ fed × 100.
**By "% Yield" is means moles $C_2ClF_3$ produced/moles $C_2Cl_3F_3$ consumed × 100.
***By "Ratio" is meant moles $C_2H_3Cl$ produced/moles $C_2ClF_3$ produced.

EXAMPLES 11-32—10 SECOND CONTACT TIME

Example 1 was repeated for the catalysts shown in Table II with the feed rates slowed down to 0.48 moles/hour for ethylene and 0.24 moles/hour of fluorocarbon 113 giving a contact time of 10 seconds. The results are displayed in Table II. It should be noted that the $\gamma AlF_3$ of Example 22 was prepared by fluorinating $Al_2O_3$ with HF at below 420° C. while the $\alpha AlF_3$ of Example 23 was prepared by fluorinating $Al_2O_3$ with HF at about 720° C. The supports of Examples 30, 31 and 32 were obtained from Girdler Chemical, Inc. of Louisville, Kentucky. Examples 14, 15, 16, 17, 20, 22, 23, 25 and 28 represent the present invention. The remaining examples (designated C) are comparative examples.

Table II

Reaction of $C_2Cl_3F_3$ And $C_2H_4$
Contact time 10 Seconds

| Example | Catalyst | Temperature | % Conversion of $C_2Cl_3F_3$ | % Yield $C_2ClF_3$ | Ratio |
|---|---|---|---|---|---|
| C11 | Sodium chloride on $Al_2O_3$ | 400 | 3 | 69 | 0.00 |
|  |  | 450 | 33 | 73 | 0.26 |
|  |  | 500 | 74 | 85 | 0.30 |
| C12 | $Al_2O_3$ alone | 400 | 16 | 21 | 0.51 |
|  |  | 450 | 39 | 47 | 0.33 |
|  |  | 500 | 61 | 93 | 0.14 |
| C13 | Copper (II) chloride on $Al_2O_3$ | 400 | 8 | 70 | 0.10 |
|  |  | 450 | 27 | 79 | 0.25 |
|  |  | 500 | 63 | 85 | 0.37 |
| 14 | Iron (III) chloride on $NaMgF_3$ | 400 | 11 | 53 | 0.12 |
|  |  | 450 | 32 | 58 | 0.34 |
|  |  | 500 | 69 | 80 | 0.44 |
| 15 | Nickel (II) chloride on $NaMgF_3$ | 400 | 2 | 91 | 0.30 |
|  |  | 450 | 17 | 68 | 0.10 |
|  |  | 500 | 50 | 79 | 0.23 |
| 16 | Vanadium chloride on $NaMgF_3$ | 400 | 4 | 71 | 0.00 |
|  |  | 450 | 57 | 95 | 0.04 |
|  |  | 500 | 62 | 81 | 0.35 |
| 17 | Iron (III) chloride and potassium chloride on $NaMgF_3$ | 400 | 20 | 84 | 0.27 |
|  |  | 450 | 27 | 80 | 0.35 |
|  |  | 500 | 68 | 84 | 0.38 |
| C18 | $NaMgF_3$ alone | 400 | 4 | 60 | 0.00 |
|  |  | 450 | 28 | 50 | 0.19 |
|  |  | 500 | 50 | 74 | 0.43 |
| C19 | Copper (II) chloride on $KMgF_3$ | 400 | 10 | 73 | 0.05 |
|  |  | 450 | 43 | 63 | 0.31 |
|  |  | 500 | 84 | 87 | 0.62 |
| 20 | Iron (III) chloride on $KMgF_3$ | 400 | 10 | 73 | 0.05 |
|  |  | 450 | 43 | 63 | 0.31 |
|  |  | 500 | 84 | 87 | 0.62 |
| C21 | Copper (II) chloride on carbon | 400 | 7 | 51 | 0.11 |
|  |  | 450 | 12 | 100 | 0.00 |
|  |  | 500 | 24 | 86 | 0.07 |
| 22 | Iron (III) chloride on $AlF_3$ | 400 | 35 | 69 | 0.61 |
|  |  | 450 | 49 | 76 | 0.57 |
|  |  | 500 | 46 | 90 | 0.39 |
| 23 | Iron (III) chloride on $AlF_3$ | 400 | 3 | 56 | 0.07 |
|  |  | 450 | 10 | 82 | 0.18 |
|  |  | 500 | 44 | 82 | 0.33 |
| C24 | Copper (II) chloride on $Cr_2O_3$ | 400 | 54 | 82 | 0.08 |
| 25 | Iron (III) chloride on $Cr_2O_3$ | 400 | 29 | 83 | 0.10 |
|  |  | 450 | 55 | 87 | 0.32 |
| C26 | $Cr_2O_3$ alone | 400 | 9 | 71 | 0.07 |
|  |  | 450 | 29 | 81 | 0.06 |
|  |  | 500 | 69 | 89 | 0.13 |
| C27 | Copper (II) chloride on NaF | 400 | 5 | 80 | 0.14 |
|  |  | 450 | 15 | 81 | 0.54 |
|  |  | 500 | 26 | 87 | 0.12 |
| 28 | Iron (III) chloride on NaF | 400 | 1 | 91 | 0.10 |
|  |  | 450 | 6 | 96 | 0.25 |
|  |  | 500 | 20 | 93 | 0.14 |
| C29 | Copper (II) chloride on Girdler T-372 Refractory Oxide | 400 | 39 | 30 | 0.55 |
|  |  | 450 | 62 | 60 | 0.41 |
|  |  | 500 | 96 | 77 | 0.35 |
| C30 | Copper (II) chloride on Girdler T-373 Refractory Oxide | 400 | 11 | 64 | 0.16 |
|  |  | 450 | 34 | 86 | 0.24 |
|  |  | 500 | 78 | 88 | 0.56 |
| C31 | Copper (II) chloride on $BaF_2$ | 450 | 10 | 87 | 0.20 |
|  |  | 500 | 26 | 96 | 0.21 |
| C32 | Copper (II) chloride on Girdler montmorillonite clay | 400 | 32 | 54 | 0.17 |
|  |  | 450 | 81 | 79 | 0.48 |

We claim:
1. A method for the dechlorination of haloethanes comprising reacting in the gaseous phase a haloethane selected from the group consisting of $CCl_2FCClF_2$, $CClF_2CClF_2$ and $CCl_2FCCl_2F$ with ethylene in the presence of a supported transition metal catalyst selected from the group consisting of iron, nickel, vanadium and chromium oxides, chlorides and fluorides and recovering a perhaloethylene and vinyl choride.

2. The method of claim 1 wherein said halohydrocarbon is $CCl_2FCClF_2$.

3. The method of claim 1 wherein said catalyst is selected from the oxides, fluorides and chlorides of iron at valence state 3.

4. The method of claim 3 wherein said catalyst is iron (III) chloride.

5. The method of claim 1 wherein said catalyst includes one of said oxides, fluorides or chlorides on an inert support, applied at a rate of between about 0.003 and about 0.30 moles of oxide, fluoride or chloride per 100 grams of support.

6. The method of claim 5 wherein said catalyst is iron (III) chloride.

7. The method of claim 6 wherein said support is gamma aluminum fluoride.

8. The method of claim 6 wherein said support is alumina or partially fluorinated alumina.

9. The method of claim 1 having contact time between about 0.3 and about 60 seconds.

10. The method of claim 1 wherein said haloethane and ethylene are fed at a molar ratio of haloethane:ethylene between about 0.1:1 and about 10:1.

11. The method of claim 10 wherein said ratio is between about 0.5:1 and about 2:1.

12. The method of claim 1 where said haloethane is $CClF_2CClF_2$.

13. The method of claim 1 wherein the reaction is conducted at between about 400° C. and about 600° C.

14. The method of claim 13 wherein the reaction is conducted at between about 400° C. and about 550° C.

15. The method of claim 14 wherein the reaction is conducted at between about 450° C. and about 500° C.

* * * * *